United States Patent
Tennakoon et al.

(10) Patent No.: US 6,795,176 B1
(45) Date of Patent: Sep. 21, 2004

(54) CONTAINER INSPECTION MACHINE

(75) Inventors: Sarath G. Tennakoon, Elmira, NY (US); Henry F. Raupp, Freeville, NY (US)

(73) Assignee: Emhart Glass S.A., Cham (CH)

(*) Notice: Subject to any disclaimer, the term of this patent is extended or adjusted under 35 U.S.C. 154(b) by 0 days.

(21) Appl. No.: 10/610,422

(22) Filed: Jun. 30, 2003

(51) Int. Cl.[7] .......................... G01N 21/00; G01N 9/04
(52) U.S. Cl. .............................. 356/239.1; 356/240.1; 250/223 B
(58) Field of Search ...................... 356/239.1, 239.4, 356/239.5, 239.6, 240.1; 250/223 B, 559.45, 559.46; 382/141, 144; 348/125, 127

(56) References Cited

U.S. PATENT DOCUMENTS

| | | | | |
|---|---|---|---|---|
| 3,770,969 A | * | 11/1973 | Ansevin et al. | 250/223 B |
| 4,908,507 A | * | 3/1990 | Imre et al. | 250/223 B |
| 4,943,713 A | * | 7/1990 | Yoshida | 250/223 B |
| 5,095,204 A | * | 3/1992 | Novini | 250/223 B |
| 5,349,435 A | * | 9/1994 | Hall et al. | 356/239.4 |
| 5,436,722 A | * | 7/1995 | Baldwin | 356/239.4 |
| 5,510,610 A | * | 4/1996 | Baldwin | 250/223 B |
| 5,717,486 A | * | 2/1998 | Burri et al. | 356/240.1 |

FOREIGN PATENT DOCUMENTS

| | | | | |
|---|---|---|---|---|
| JP | | 401243193 A | * | 9/1989 |
| JP | | 406341963 A | * | 12/1994 |

* cited by examiner

Primary Examiner—Hoa Q. Pham
(74) Attorney, Agent, or Firm—Spencer T. Smith

(57) ABSTRACT

A machine for inspecting the heal code of a bottle. The bottle is supported vertically at an inspection location and a camera having an imaging area is located vertically beneath the bottle. A light source directs a beam of light downwardly through the bottle and an iris for limits the beam to light which pass through the opening of the supported bottle and will illuminate the bottom of the supported bottle outwardly to the heal code of the bottle. A cylindrical mirror is supported coaxial to the axis of the bottle between the bottom of the bottle and the camera for reflecting an annular beam of light containing the heal code towards the camera, and a transparent plate having a black center prevents light within the annular beam of light from reaching the camera.

2 Claims, 2 Drawing Sheets

CONTAINER INSPECTION MACHINE

The present invention relates to machines which inspect bottles for defects and more particularly to a system for inspecting the heal code at the bottom of a bottle.

BACKGROUND OF THE INVENTION

Machines for inspecting glass bottles correlate defects with mold cavity so that an operator will know where a defective bottle was made and can promptly adjust the bottle making process to eliminate the problem at that mold. Mold data in the form of raised dots of glass are often present on the outer wall of the bottle just above the bottom of the bottle (a heal code). These glass dots generally are located in a common horizontal plane.

OBJECT OF THE INVENTION

It is an object of the present invention to provide a machine for inspecting glass containers which can read a heal code on a bottle.

Other objects and advantages of the present invention will become apparent from the following portion of this specification and from the accompanying drawings which illustrate, in accordance with the mandate of the patent statutes, a presently preferred embodiment incorporating the principles of the invention.

BRIEF DESCRIPTION OF THE PREFERRED EMBODIMENT

Figure 1:
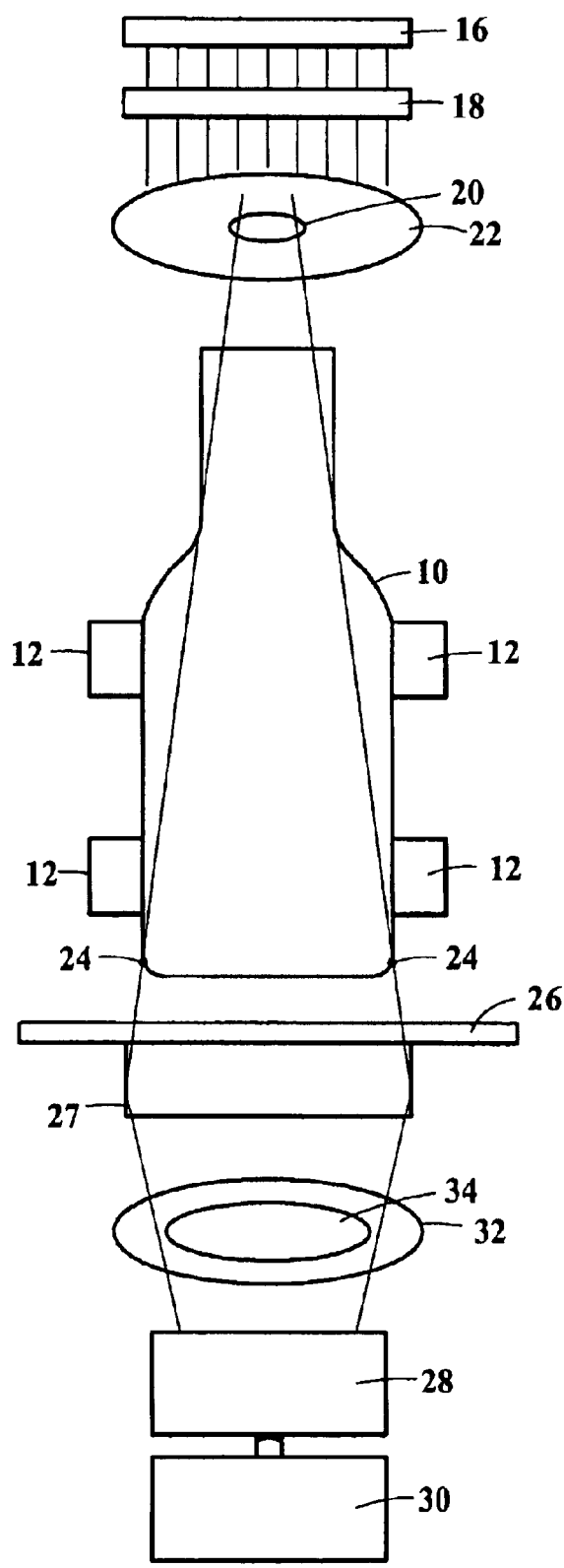
FIG. 1 is an elevational schematic view of a system for inspecting the bottom of a bottle for defects.
Figure 2:
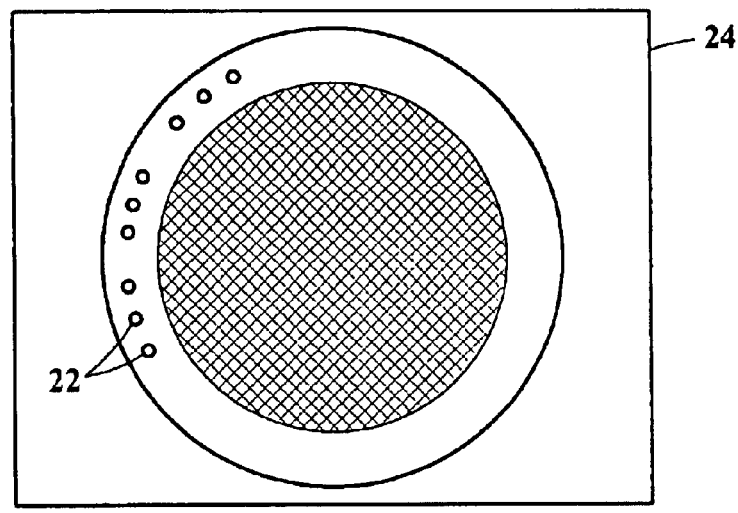
FIG. 2 is a schematic showing of the camera image of a heal code.

A bottle 10 is supported at an inspection station by opposed pairs of drive belts 12. Above the top of the bottle is located a light source 16 in the form of an L.E.D. light board (a square matrix of L.E.D's). The emitted light is diffused by a diffuser 18 and then passes through the opening 20 of an iris 22. The opening is selectively sized to permit light to pass through the opening of the bottle and flow downwardly to illuminate the bottom of the bottle outwardly to the sidewall of the bottle above the base where nubs of glass 24 are present representing coded information pertinent to the bottle (a heal code).

The light passes through the bottle and then the annular beam corresponding to the beam of light which has passed through the bottle proximate the heal code, will be reflected as an annular beam by a cylindrical mirror 27 which is located between the bottom of the bottle and the camera towards a wide angle lens of an imaging camera 28 (a Fresnel lens 26 can be located between the cylindrical mirror and the bottom of the bottle to reduce the diameter of the light beam). A plate 32 having a circular black center 34 is located between the cylindrical mirror and the imaging surface of the camera. The size of the circular black center is defined so that light other than the annular beam containing the heal code will be prevented from reaching the imaging surface of the camera. The image will be evaluated by a processor 30. If desired the iris could be automated and the light source and diffuser could be part of a vertically displaceable unit.

What is claimed is:

1. A machine for inspecting the heal code of a round bottle having an axis comprising means for supporting a bottle vertically at an inspection location, a camera having an imaging area vertically beneath a bottle supported at the inspection location, light source means for directing a beam of light downwardly through the bottle, an iris having a circular opening selectively sized for limiting the beam of light to light which passes through the opening of the supported bottle and illuminates the bottom of the supported bottle outwardly to the heal code area of the bottle, a cylindrical mirror coaxial to the axis of the bottle for reflecting an annular beam of light containing the heal code towards said camera, and a transparent plate located between the cylindrical mirror and said camera having a black circular center for preventing light within the annular beam of light from reaching the camera.

2. A machine for inspecting the heal code of a bottle according to claim 1, wherein said light source means comprises a L.E.D. light board and a diffuser.

* * * * *